United States Patent [19]
Osborne et al.

[11] Patent Number: 5,312,347
[45] Date of Patent: May 17, 1994

[54] HYPODERMIC NEEDLE SHIELD

[76] Inventors: Barbara J. Osborne, 4184 SE. Centerboard La., Stuart, Fla. 34997; Richard W. Slawson, 211 S. Beach Rd., Hobe Sound, Fla. 33455

[21] Appl. No.: 21,218

[22] Filed: Feb. 23, 1993

Related U.S. Application Data

[63] Continuation-in-part of Ser. No. 843,354, Feb. 27, 1992, abandoned.

[51] Int. Cl.$^5$ .............................................. A61M 5/00
[52] U.S. Cl. .................................... 604/110; 604/198; 604/263
[58] Field of Search ............... 604/110, 187, 192, 198, 604/263

[56] References Cited

U.S. PATENT DOCUMENTS

| | | |
|---|---|---|
| Re. 33,585 | 5/1991 | Haber et al. . |
| 4,573,976 | 3/1986 | Sampson et al. . |
| 4,666,435 | 5/1987 | Braginetz . |
| 4,693,708 | 9/1987 | Wanderer et al. . |
| 4,702,738 | 10/1987 | Spencer . |
| 4,723,943 | 2/1988 | Spencer . |
| 4,813,940 | 3/1989 | Parry ........................ 604/263 X |
| 4,816,022 | 3/1989 | Poncy . |
| 4,826,490 | 5/1989 | Byrne et al. . |
| 4,840,185 | 6/1989 | Hernandez . |
| 4,842,587 | 6/1989 | Poncy . |
| 4,861,338 | 8/1989 | Mathiesen et al. . |
| 4,892,523 | 1/1990 | Haber et al. . |
| 4,915,702 | 4/1990 | Haber . |
| 4,943,282 | 7/1990 | Page et al. . |
| 4,943,283 | 7/1990 | Hogan . |
| 4,961,730 | 10/1990 | Poncy . |
| 4,976,701 | 12/1990 | Ejlersen et al. . |
| 5,011,479 | 4/1991 | Le et al. . |
| 5,061,251 | 10/1991 | Juhasz . |
| 5,098,403 | 3/1992 | Sampson ........................ 604/198 |
| 5,104,384 | 4/1992 | Parry . |
| 5,181,524 | 1/1993 | Wanderer et al. ............... 604/198 X |

Primary Examiner—John D. Yasko
Attorney, Agent, or Firm—Pearne, Gordon, McCoy & Granger

[57] ABSTRACT

A detachable needle assembly is provided with a needle shield supported for telescoping movement on the needle hub, with the sliding-fit surface on which the shield moves being separated by a majority of the cross-section of the hub from the feed passage through the hub, or with the shield being movable over an end portion of the hub on which a cover cap is supported prior to use.

20 Claims, 4 Drawing Sheets

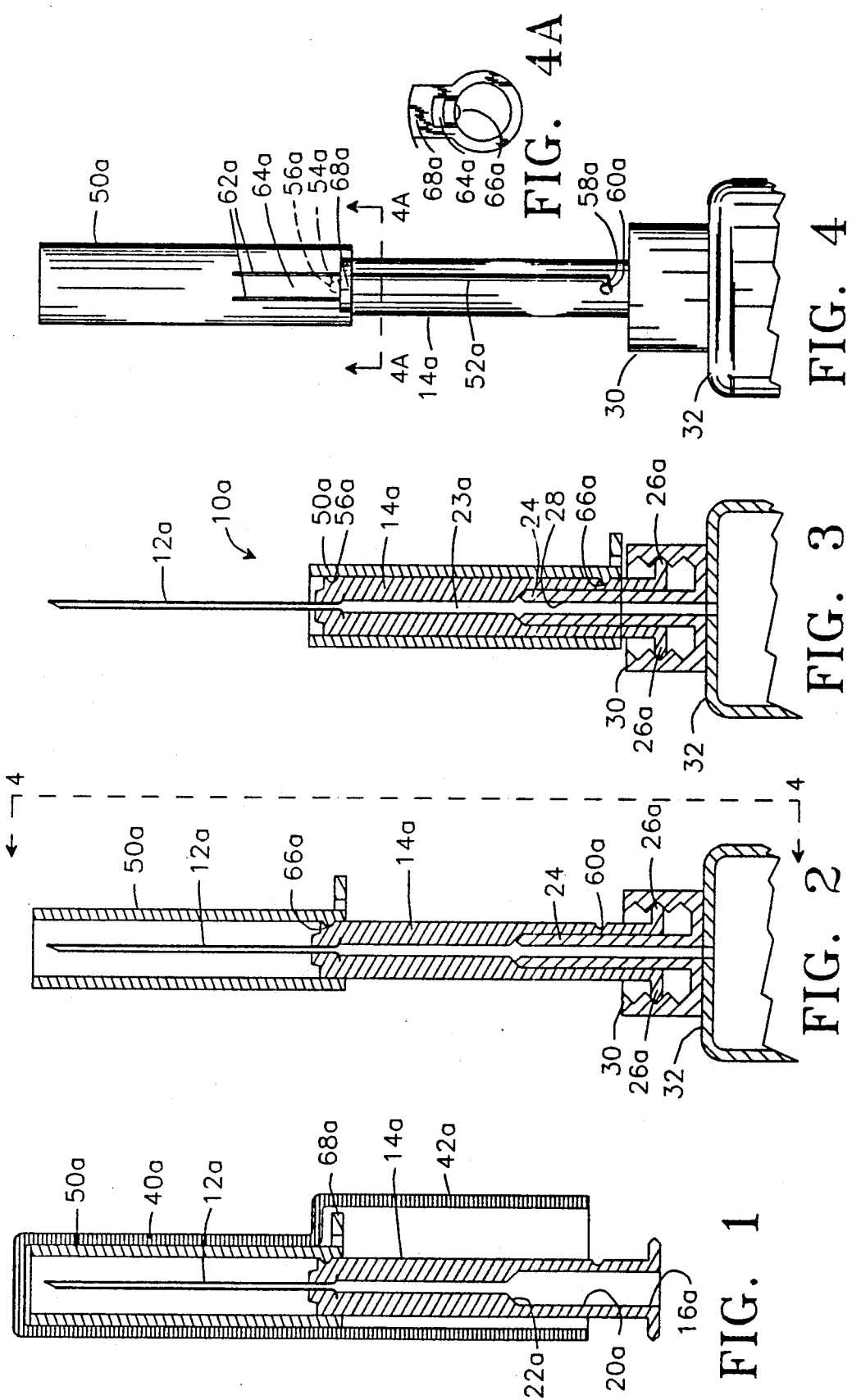

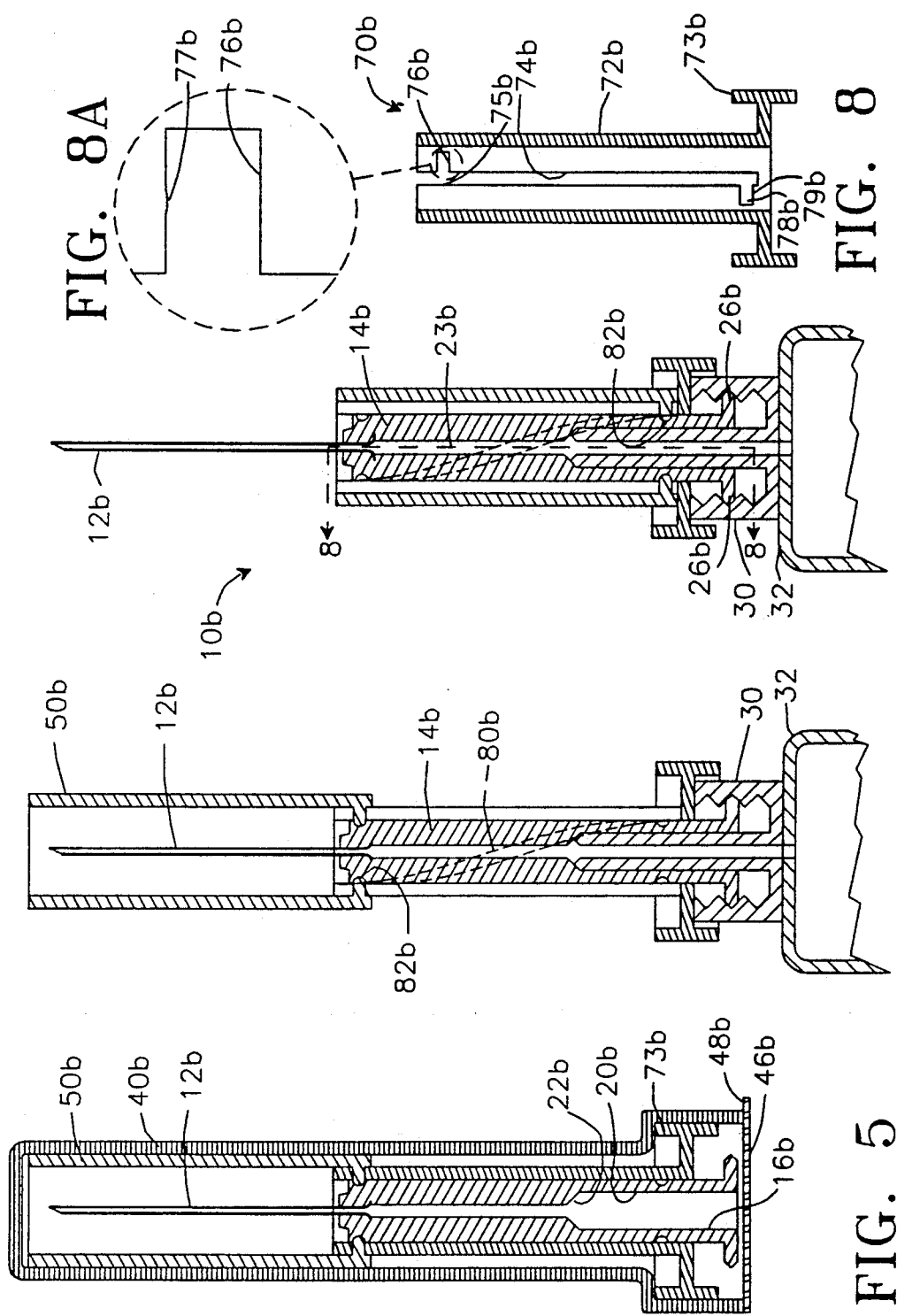

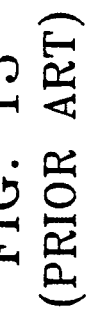
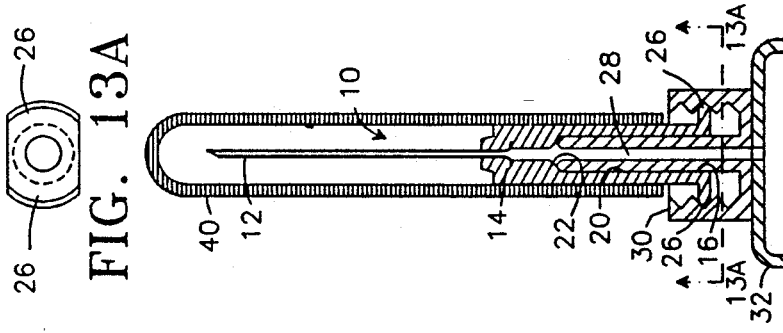
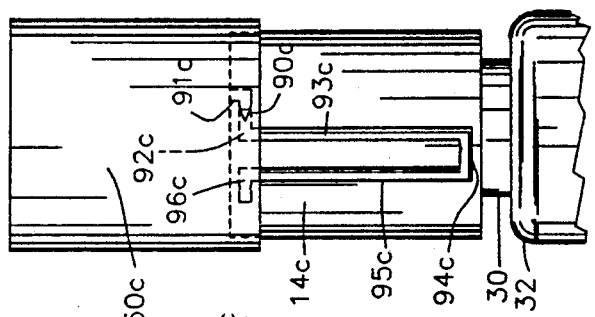
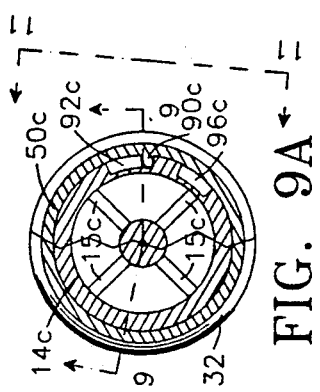
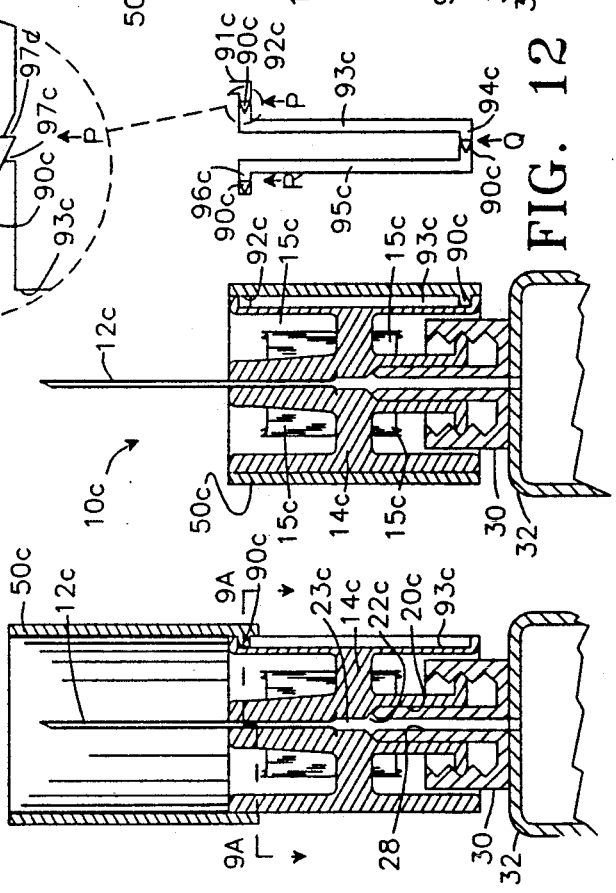

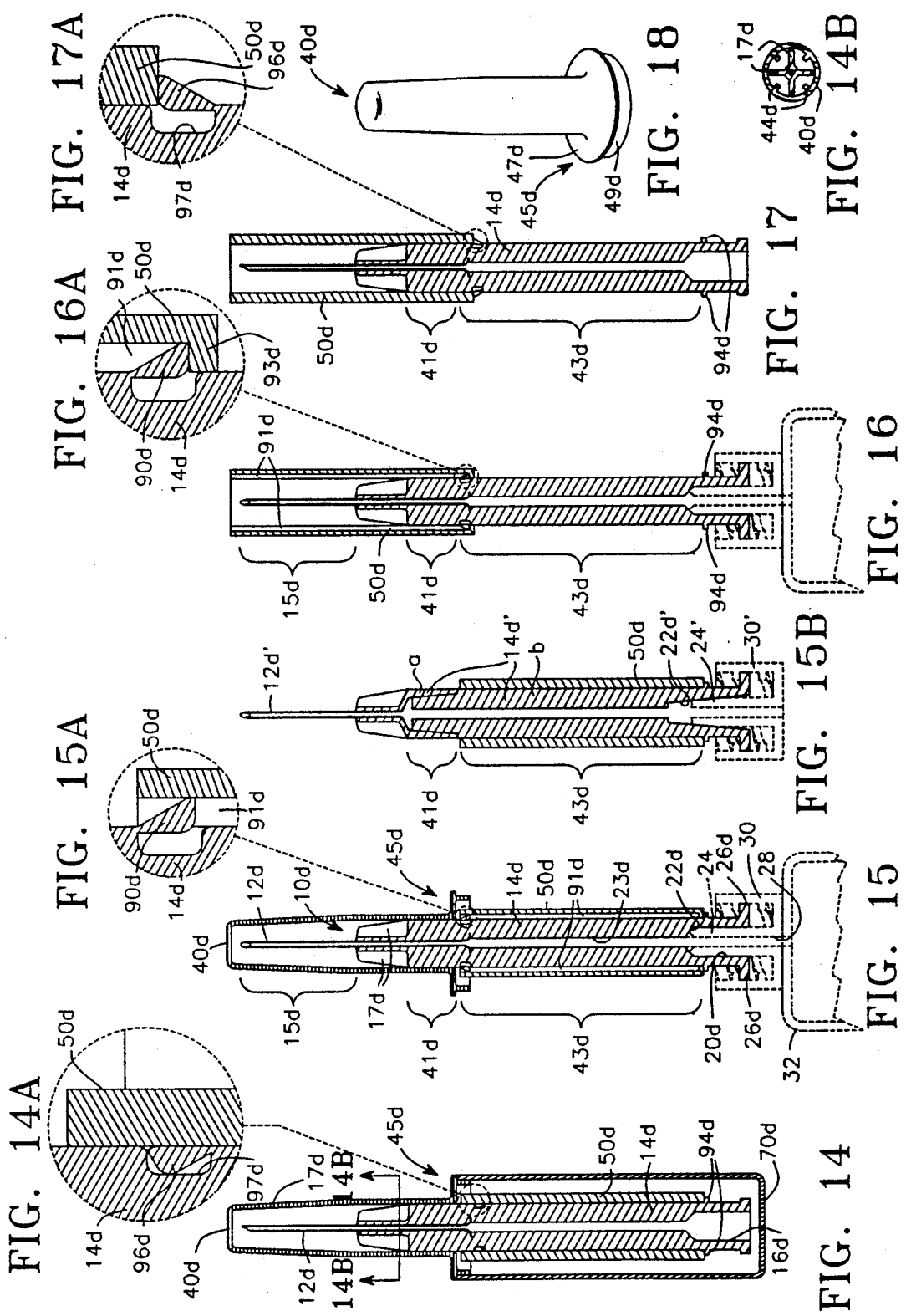

HYPODERMIC NEEDLE SHIELD

This application is a continuation-in-part of application Ser. No. 07/843,354 filed Feb. 27, 1992 now abandoned.

This invention relates to "safety" detachable syringe needles which can be safely used and discarded with minimal chance of accidental pricking of a finger or other body part of the nurse or other health care worker handling the syringe and attending to its use.

There is a manifest need for safety syringe needles, as evidenced by a number of patents issued in recent years which are directed to the problem of preventing accidental pricking. The increasing incidence of AIDS and the presence of other serious infectious diseases have stimulated the effort to provide an acceptable safety syringe needle that is practical. Various proposals for providing a protective extendible needle shield are set forth in the following patents, among others:

| | |
|---|---|
| Haber et al. | Re. 33,585 |
| Sampson et al. | 4,573,976 |
| Braginetz | 4,666,435 |
| Wanderer et al. | 4,693,708 |
| Spencer, Treesa A. | 4,702,738 |
| Spencer, John E. | 4,723,943 |
| Poncy | 4,816,022 |
| Byrne et al. | 4,826,490 |
| Hernandez | 4,840,185 |
| Poncy | 4,842,587 |
| Mathiesen et al. | 4,861,338 |
| Poncy | 4,961,730 |
| Haber et al. | 4,892,523 |
| Haber, Terry | 4,915,702 |
| Hogan | 4,923,283 |
| Page et al. | 4,943,282 |
| Ejlersen et al. | 4,976,701 |
| Le et al. | 5,011,492 |
| Juhasz, Paul R. | 5,061,251 |
| Parry | 5,104,384 |

Several of the these patents relate to hub-supported shields. In U.S. Pat. No. 4,826,490 to Byrne et al., an extensible shield is slidingly supported on a hub of hollow cross-section such that the majority of the cross-section contains fluid being injected, thus presenting a potential of overdose, particularly when small dosages are administered in small syringes. In the three patents to Poncy listed above, an extensible shield is slidingly supported on a hub and retracts over the syringe with which the needle is used, the range of movement necessary to cover the needle being considerably more than the length of the hub sliding surface, so that the shield must be wider than the syringe with which the needle is used, and the device is bulky and, even so, is not universal to all usual sizes of syringe. In U.S. Pat. No. 5,011,479 to Le et al., an extensible shield is slidingly supported on a double-connector intermediate member that is affixed through a first connector to the needle and through a second connector to the syringe. The health care worker must make two connections, as described at col. 4, lines 51 ff. In U.S. Pat. No. 5,104,384 to Parry, an extensible shield is mounted radially within an outer sleeve which is fixed to the hub and longitudinally extends therefrom over about half the unsupported length of the needle. This arrangement only allows the extensible shield to be withdrawn from approximately half the unsupported length of the needle, so that the unsupported length of the needle is about twice the usable (insertable) needle length, resulting in either a flimsy arrangement or a usable needle length that is impractically short.

U.K. Patent 924,734 to Linder (not listed above) is of interest since it shows a hub supported extensible barrel element which is part of a spring-powered needle projecting system. Linder's barrel does as a shield but on the contrary remains stationary while the needle advances, and leaves the needle tip exposed after use. Furthermore, assuming that Linder's barrel can be said to "retract" when it, while stationary, experiences relative advancement of the needle, such "retraction" exposes no more than a fraction of the length of the needle, which would be an impractical arrangement for an extensible needle shield.

Extensible shields for syringe needles which are not hub-mounted have also been provided, and further demonstrate the felt need there has been for practical and widely acceptable safety syringe needles. The remainder of the patents listed above are generally in this category. In U.S. Pat. No. 4,666,435 to Braginetz, a extensible needle shield is mounted on a syringe vial. In U.S. Pat. No. 4,840,185 to Hernandez, a shield is provided on the barrel of the vacuum tube holder which itself forms an extension of the syringe barrel. In U.S. Pat. No. 4,861,338 to Mathiesen et al., a needle shield is a continuation of the syringe barrel, and the needle holder is turned by the syringe plunger to advance and retract the needle. In U.S. Pat. No. 4,976,701 to Ejlersen et al., a double ended needle is shielded by a cap fixed to the "cartridge 11, 14, 15" by an "intermediate member" having a "rear part 23" and a "front part 24", or the cap 65 is threaded on the cartridge jacket 50, so that essentially the shield is an extension of the cartridge barrel. In U.S. Pat. No. 4,923,283 to Hogan, in which the needle is used in a tubing arrangement rather than with a syringe, a needle shield slides down the flexible tubing and over the needle.

Most of the foregoing patents represent efforts to respond to the need for an acceptable safety syringe needle that is practical—a safety device of simple design, one which is convenient to manipulate and use, requires little or no training, and does not materially affect dosage amounts even for syringes of the smallest sizes.

The present invention provides such a device. The present invention provides a device whose manner of use will be self-evident and natural to nurses and other medical workers. The invention provides a device which may be used without modification of syringes already widely in use, and does not materially affect accuracy of dosage even when used with syringes of the smallest sizes. In one preferred version, the invention is so perfectly in accord with present nursing practice that it requires no departure whatsoever from procedures that are presently widely used, other than simply advancing a shield when a needle is withdrawn from the patient.

An accepted and widely used hypodermic syringe design uses detachable needles which are supplied in sterile packages and are adapted to be attached to any one of a number of sizes of syringe barrels by a standard coupler or end connection provided at the distal end of each syringe. A commercial example is the "Luer-Lok" needle sold commercially Becton Dickinson & Company. The syringe-associated coupler members for receiving the needles may be constant or standard in size for various sizes of syringes, so that one of the detachable needles can be attached to a syringe of any size.

A feature of the present invention is the provision of a retractable shield associated with such detachable needles for hypodermic syringes. The design of the parts is such is such that the shield and detachable needle together provide a self-contained assembly or package that is independent of the syringe to which the needle is mounted, while at the same time being conveniently usable on all sizes of syringe from the smallest to the largest without compromise of dosage accuracy. It is not necessary to make two connections. The retracted shield can uncover the entire unsupported length of the needle, so that the needle's unsupported length need be no greater than its usable length, making for a sturdy arrangement that does not impractically restrict the usable length of the needle.

The objects and advantages of the invention will become clearer from the following description of specific embodiments, and from the accompanying drawings, in which:

FIG. 1 is a somewhat schematic cross-sectional view of a detachable needle assembly contemplated by the invention shown locked in shield-extended position and further shown in association with a partially enclosing plastic shell or cover.

FIG. 2 is a similar view of the same device coupled to a syringe and with the plastic shell or cover removed. As shown, the shield is still locked in shield-extended position.

FIG. 3 is a similar view showing the needle shield of FIG. 2 in retracted position.

FIG. 4 is a side elevation taken from the plane of line 4—4 in FIG. 2.

FIG. 4A is an end view of only the shield elements shown in FIG. 4 (the needle hub elements shown in FIG. 4 are omitted) taken from the plane of line 4A—4A in FIG. 4.

FIG. 5 is a somewhat schematic cross-sectional view of another detachable needle assembly contemplated by the invention shown locked in shield-extended position and further shown in association with an all-enclosing plastic shell or cover. FIG. 5 omits any showing of the helical grooves associated with the illustrated needle hub.

FIG. 6 is a similar view of the same device as shown in FIG. 5 coupled to a syringe and with the plastic shell or cover removed and the driver partly rotated from the locked position of FIG. 5 to the point where the driver is about to start moving downwardly in the shield-retracting direction.

FIG. 7 is a similar view showing the needle shield of FIG. 6 in fully shield-retracted position but not yet locked therein.

FIG. 8 is a cross-sectional view of only the driver elements shown in FIG. 7 (the coupler elements, hub elements and shield elements shown in FIG. 7 are omitted) taken from the plane of line 8—8 in FIG. 7.

FIG. 8A is a view on an enlarged scale of a small portion of FIG. 8.

FIG. 9 is a somewhat schematic cross-sectional view of a third detachable needle assembly contemplated by the invention shown affixed to a syringe and shown while still in shield-extended position but just after it has been unlocked from that position and is about to be moved to shield-retracted position.

FIG. 9A is a broken cross-sectional view taken from the planes of staggered line 9A—9A in FIG. 9.

FIG. 10 is a view similar to FIG. 9 showing the same needle assembly in shield-withdrawn position but not yet locked in that position.

FIG. 11 is a view taken from the plane of line 11—11 in FIG. 9A.

FIG. 12 is a diagram of the guide groove and groove follower of the illustrated embodiment, showing three locked positions of the groove follower.

FIG. 12A is a view on an enlarged scale of a small portion of FIG. 12.

FIG. 13 is a somewhat schematic cross-sectional view of a detachable needle assembly illustrative of the prior art, shown attached to a syringe but prior to removal of a plastic shell or cover associated with the detachable needle.

FIG. 13A is an end view of only the hub elements shown in FIG. 13 (the coupler elements and plastic shell or cover elements shown in FIG. 13 are omitted) taken from the plane of line 13A—13A in FIG. 13.

FIG. 14 is a somewhat schematic cross-sectional view of another detachable needle assembly felt to be particularly advantageous, shown in packaged condition with a cover body as well as a cover cap to furnish a complete package if desired.

FIG. 14A is a view on an enlarged scale of a small portion of FIG. 14.

FIG. 14B is a view taken on the plane of line 14B—14B in FIG. 14.

FIG. 15 is a cross-sectional view taken on a plane 90 degrees removed from that of FIG. 14, and showing the cover body removed and the remainder of the device affixed to a syringe by a Luer lock type connection.

FIG. 15A is a view on an enlarged scale of a small portion of FIG. 15.

FIG. 15B is a cross-sectional view of a detachable needle assembly very similar to that shown in FIG. 15, and With the parts similarly positioned (except for the omission of a cover cap), illustrating certain alternatives as to hub fabrication and connector fittings. For simplicity, FIG. 15B is not as a counterpart of FIG. 15 as shown, but of FIG. 15 as it would have appeared if viewed on a plane 45 degrees removed from the viewplane of FIG. 15. By this rotation of viewplane, there is no inconsistency in the fact that FIG. 15B does not show any detents equivalent to any of those shown in other figures.

FIG. 16 is a view on the same plane as FIG. 15 showing the cover cap removed and the needle shield extended.

FIG. 16A is a view on an enlarged scale of a small portion of FIG. 16.

FIG. 17 is a view taken on the same plane as FIG. 14 also showing the needle shield extended, and showing the device optionally disconnected from the syringe.

FIG. 17A is a view on an enlarged scale of a small portion of FIG. 17.

FIG. 18 is a sketch of the cover cap.

Drawings are referred to above as being somewhat schematic because no attempt has been made to portray mold draft angles, reinforcing ribs, precise relations as to relative wall thicknesses, and like details which persons skilled in the art of injection molding or other appropriate manufacturing methods may utilize as a matter of routine design.

For a better understanding of the invention, detachable needles of the prior art will first be described. These may be of the type illustrated by the detachable needle generally indicated by the reference numeral 10 in FIG. 13. The detachable needle 10 includes a needle proper 12 and a needle hub 14. The needle is anchored to the hub and extends coaxially from the distal end of the hub. An open mouth 16 in the proximal or lower end of the hub provides inlet means for fluids passing through the hub. The mouth 16 also forms a bore 20 extending upwardly to a seat 22 for receiving a hollow male coupler member 24 which has a central passage 28. The seat 22 provides interior annular socket means for the male coupler member 24. The member 24 is integrally formed as part of the coupler generally indicated by the reference numeral 30. The coupler 30 is a standardized fitting or coupler member fixed to the end of syringe barrel 32. The syringe barrel may have any one of a number of standard diameters, ranging from a diameter only slightly larger than male member 24 of the fitting 30 up to four or more times the outside diameter of fitting 30. The hub 14 also has a radially extending flange means comprising a pair of radially extending flanges 26 adapted to threadedly engage the interior threads 34 of fitting 30. When the flanges 26 are turned down in the threads 34, the male coupler member 24 is tightened into the seat 22, and the central passage 28 is sealingly connected to the hub passage 23 which leads to the needle 12. Sometimes the parts are proportioned such that the penetration of the male member is limited by bottoming of the flanges in the threaded part of the fitting rather than by bottoming of the male member on a seat or lengthwise taper fit (not shown in FIG. 13, but see taper fit of male member 24' of fitting 30' in FIG. 15B, to be later described and illustrating a device contemplated by the present invention used with such a fitting), which may still give an adequate seal if the fit of the male member in the bore is sufficiently close, i.e., is a good "press fit." Syringes of smallest diameter are not provided with the threaded female part of the connector fitting, but only with the male member, and sealing must be accomplished by pushing the parts together lengthwise rather than twisting them to tighten down a threaded connection. When this is the case, a gentle taper fit may be preferable to the seating illustrated in FIG. 13 or to a press fit arrangement in which the male member does not bottom.

A plastic shell or cover cap 40 is provided which may have a slightly tapered fit (not shown in FIG. 13) on the hub 14 such that the cover 40 is spaced above the needle when seated as far as possible on upper or distal end of the hub in the position shown in FIG. 13. Prior to use, and prior to being coupled to a syringe, the assembly as so far described (of course excluding the coupling 30 and syringe barrel 32) may be supplied in a sterile flexible package or envelope (not shown).

When the detachable needle is to be used, the user removes the sterile assembly from its sterile packaging, grasps the shell or cover 40 in the vicinity of the hub 14, and connects the assembly to a syringe 32 by inserting the flanges 26 into the threads 34 of the syringe coupler 30 and twisting the hub to tighten the flanges down in the threads until the male member 24 of the coupler is received tightly in the seat 22. When the detachable needle is tightly coupled to the syringe, the plastic shell or cover is removed by twisting and pulling it off the hub.

When the worker grasps the cover 40 in the vicinity of the hub 40, sterility at this location on the cover is destroyed, but that is of no consequence, since sterility of the detachable needle and of the interior passages between the syringe and the needle tip is preserved.

Following uncovering of the needle, medication may be aspirated into the syringe. If this is done at a point remote from the patient, the cover 40 (the interior of which is still sterile at this point) may be replaced on the distal or upper end of the hub 14 to temporarily re-cover the needle and protect needle sterility until use, the cover of course being again removed prior to injection of the medication. If it is not necessary to protect the sterility of the needle between aspiration of medication and medication, the needle is not temporarily re-covered between these steps.

Following use, the needle is no longer sterile. If the needle is not shielded following use, obviously a risk is presented to health care personnel and others required to handle or dispose of the used devices. Following use, the needle 12 may be again re-covered with the cover 40 (which, inconveniently, has to have been saved when originally removed) by applying the cover over the "front" or distal end of the needle. Doing so involves moving the cover in the proximal direction while the cover is closely adjacent the needle tip and, moreover, involves moving the cover over the needle from beyond the needle tip, thereby presenting a substantial risk of a needle prick to a possibly harried and distracted health care worker.

If the needle is to be detached from the syringe following use, the user must either proceed while the needle is still exposed by grasping the hub and twisting it in order to back the flanges 26 out of the threads 24, thereby risking a prick from the exposed needle during such backing-out, or must re-cover the needle in the manner previously described, with the attendant risk of pricking at that stage.

The invention presents a needle which may be safely shielded before and after use by shield means which is conveniently manipulated solely from the proximal end of the needle assembly, thus avoiding direct exposure to the needle tip or any need to grasp parts located beyond the needle tip. At the same time, the present invention may be used in place of the detachable needles of the prior art with little or no modification of the practices of the prior art in using needles of that general type, and without modification of existing syringes used with detachable needles.

An embodiment of the invention is shown in FIGS. 1-4. A detachable needle generally indicated by the reference numeral 10a (FIG. 3) includes a needle proper 12a and a needle hub 14a. The hub 14a is somewhat elongated and preferably of generally cylindrical configuration. The needle 12a is anchored to the hub 14a and extends coaxially from the distal end of the hub. An open mouth 16a (FIG. 1) in the proximal or lower end of the hub provides inlet means for fluids passing through the hub. The mouth 16a also forms a bore 20a extending upwardly to a seat 22a for receiving the hollow male coupler member 24 associated with a standard coupler 30 of the type previously described. The seat 22a provides interior annular socket means for the male coupler member 24.

The hub 14a also has radially extending flange means comprising a pair of radially extending flanges 26a adapted to threadedly engage the interior threads of fitting 30. The flanges 26a and seat 22a comprise means for screw-down connection with the standard coupler 30. When the flanges 26a are turned down in the threads, the male coupler member 24 is tightened into the seat 22a, and the central passage 28 of the male coupler member is sealingly connected to the hub passage 23a which leads to the needle 12a, to establish a fluid flow path whose cross-sectional area along almost all, if not all, its longitudinal extent within the hub is a minority of the cross-sectional area of the hub itself.

The detachable needle assembly 10a is provided with a shield or shroud 50a which is slidingly supported on the hub 14a for telescoping movement between needle-covering or shield-extended position seen in FIGS. 1, 2 and 4 and needle-exposing or shield-retracted position seen in FIG. 3. In the shield-retracted position, preferably the entire length of the needle outside the hub is exposed, as shown. The portion of the cylindrical exterior of the hub that is underneath the shield constitutes a sliding-fit surface on which the shield is supported in its telescoping movement, and the longitudinal extent of such sliding-fit surface is substantially no less than the distance of travel of the shield between extended and retracted positions. Such sliding fit-surface is not necessarily continuous, but can be interrupted by lightening holes, grooves, chambers, or the like (not shown) for material and weight saving, if desired.

It is to be noted that all points of support of the shield 50a on the hub 14a are themselves supported entirely via the engagement of the screw-down connection means of the detachable needle assembly with the syringe-mounted locking means 30, and that such telescoping support is self-established by the detachable needle assembly and does not depend to any significant degree, or to any degree whatsoever in the illustrated embodiment, on structural support or interaction of the shield with any elements associated with the syringe 32. Thus, the telescoping support of the needle shield 50a on the needle hub 14a is a substantially self-established attribute of the detachable needle assembly 10a. It is further to be noted that the shield 50a, along its length when in its retracted position, is radially spaced, by the majority of the cross-sectional area of the hub, from corresponding lengthwise portions of the fluid flow path that is established by passages 23a and 28.

Suitable detent, guide and tab means may be provided to hold the shield in its extended or retracted position, to guide its movement between extended and retracted positions, and to allow it to be conveniently manually actuated from the proximate end of the detachable needle assembly. In the illustrated example, a longitudinal groove 52a (FIG. 4) is formed in the outer wall of the needle hub 14a. The longitudinal groove 52a is joined at its outer end to a short lateral groove 54a terminating in a slight depression 56a. The longitudinal groove 52a is joined at its inner end to a short lateral groove 58a terminating in a slight depression 60a.

The shield 50a is preferably of hollow cylindrical shape as shown, and is the illustrated example has a pair of slits 62a extending from its lower or proximal end. The slits 62a define a spring tab 64a. A groove follower or detent projection 66a is formed on the inner side of the spring tab 64a near its free end. The dimensions of these parts are such that the spring tab 64a is slightly spring-loaded when the detent projection 66a is positioned in the depression 56a or 60a, and is spring-loaded to a slightly greater extent when the detent is positioned in the longitudinal groove 52a or in one of the short lateral grooves 54a or 58a.

As best seen in FIG. 4A, the shield 50a is also provided with an integral control tab 68a which is spaced above and bridges the end of the spring tab 64a in such a manner as not to interfere with the springing action of the tab 64a as best shown in FIG. 4A.

The construction as so far described may be supplied in a plastic shell or cover 40a (FIG. 1). The cover may be enlarged at portion 42a to allow its removal past the control tab 68a. The filleted corners at the top end of the cover may snugly fit against the extended shroud or shield 50a, as shown in FIG. 1. The construction as thus far described may be contained in a flexible sterile package (not shown).

When the detachable needle of FIGS. 1-4 is to be used, the user removes the sterile assembly from its sterile packaging, grasps the cover 40a in the vicinity of the top end of the hub 14a, and connects the assembly to a syringe 32 by inserting the flanges 26a into the threads of the syringe coupler 30 and twisting the hub to tighten the flanges down in the threads until the male member 24 of the coupler is received tightly in the seat 22a. When the detachable needle is tightly coupled to the syringe, the plastic shell or cover is removed by twisting and pulling it off the shroud or shield 50a, leaving the needle in covered or protected condition as illustrated in FIGS. 2 and 4.

When the health care worker grasps the cover 40a in the vicinity of the top end of the hub 14a, sterility at this location on the cover is destroyed, but as is similarly true of the detachable needles of the prior art described above, that is of no consequence, since sterility of the detachable needle and of the interior passages between the syringe and the needle tip is preserved.

It is noteworthy that the manipulations used to connect the detachable needle of the invention to a syringe are very similar to, if they do not exactly duplicate, the manipulations used to connect the detachable needles of the prior art which are described above. Health care workers already familiar with the use of detachable needles require little or no training before they can proceed with confidence to properly connect the detachable needle of the convention. Also to be noted is the fact that the invention can be used with the same syringes as have been used with the detachable needles of the prior art, without any modifications of such known types of syringes.

When the detachable needle 10a is supplied and is in the condition shown in FIG. 1, the detent projection 66a is positioned in the depression 56a and the shield 50a is locked against retraction. After the detachable needle 10a is coupled to a syringe and the cover 40a is removed, the needle may be exposed by pushing the control tab 68a with a finger to move the detent projection 66a out of the depression 56a and into the short lateral groove 64a. This move will encounter a resistance due to the fact that the depression 56a is slightly deeper than the groove 64a, but the resistance can be overcome with firm finger pressure on the control tab 68a to torque the shield 50a and start the motion. Once the detent projection 66a is in the groove 54a it is moved along that groove with relatively little resistance by continuing the torquing of the shield 50a until the projection 66a reaches the upper or distal end of the longitudinal groove 52a. The control tab 52a is then finger-pulled longitudinally to move the projection 66a downwardly from the distal to the proximate end of the groove 52a, again with relatively little resistance. This of course pulls the entire shield 50a to retracted or needle-exposing position. The shield can then be locked in retracted position by lightly torquing the shield by finger pressure on the control tab 68a to move the detent projection 66a along the short lateral groove 58a and into the depression 60a.

While the foregoing description of the retracting motions is very detailed, the motions themselves are simple and can be performed in a straightforward and simple manner using a single finger or using the thumb and index finger to manipulate the control tab 68a in a manner that is obvious to the user, or is easily learned if not self-evident.

After the needle has been used, or after aspiration of medicine prior to use, the shield 50a can be extended to needle covering position by reversing the motions just described. The shield is released from its locked retracted position by finger-applied torquing pressure sufficient to force the detent projection 66a out of the depression 60a against a resistance that is due to the fact that the depressions 60a is deeper than the longitudinal groove 58a leading from the depression. The remainder of the motion is the reverse of that previously described and should be self-evident.

It is noteworthy that all manipulations described ar performed, so to speak, from the "back" or proximate end of the needle assembly, and the fingers never move past the needle tip, or anywhere close to the needle tip, and never move from a point beyond or in front of the needle tip, but are at all times well away from and "behind" the needle tip.

Another embodiment of the invention is shown in FIGS. 4–8. A detachable needle generally indicated by the reference numeral 10b (FIG. 7) includes a needle proper 12b and a needle hub 14b. The hub 14b is somewhat elongated and preferably of generally cylindrical configuration. The needle 12b is anchored to the hub 14b and extends coaxially from the distal end of the hub. An open mouth 16b (FIG. 5) in the proximal or lower end of the hub provides inlet means for fluids passing through the hub. The mouth 16b also forms a bore 20b extending upwardly to a seat 22b for receiving the hollow male coupler member associated with a standard coupler 30 of the type previously described. The seat 22b provides interior annular socket means for the male coupler member.

The hub 14b also has radially extending flange means comprising a pair of radially extending flanges 26b adapted to threadedly engage the interior threads of fitting 30. When the flanges 26b are turned down in the threads, the male coupler member is tightened into the seat 22b, and the central passage of the male coupler member is sealingly connected to the hub passage 23b which leads to the needle 12b, to establish a fluid flow path whose cross-sectional area along almost all, if not all, its longitudinal extent within the hub is a minority of the cross-sectional area of the hub itself.

The detachable needle assembly 10b is provided with a shroud or shield 50b which is slidingly supported on the hub 14b for telescoping movement between needle-covering or shield-extended position seen in FIGS. 5 and 6 and needle-exposing or shield-retracted position seen in FIG. 7. In the shield-retracted position, preferably the entire length of the needle outside the hub is exposed, as shown. In the illustrated example, the sliding telescoping support of the shield 50b on the hub 14b is not by direct contact between the members 50b and 14b, but is via an intermediate driver member 70b, most clearly seen in FIG. 8, which will be more fully described below. The portion of the cylindrical exterior of the driver member that is underneath the shield constitutes a sliding-fit surface which is supported by the hub and on which the shield is supported in its telescoping movement, and the longitudinal extent of such sliding-fit surface is substantially no less than the distance of travel of the shield between extended and retracted positions. Such sliding fit-surface is not necessarily continuous, but can be interrupted by lightening holes, grooves, chambers, or the like (not shown) for material and weight saving, if desired.

It is to be noted that all points of support of the shield 50b on the hub 14b (via the driver member 70b) are themselves supported entirely via the engagement of the screw-down connection means of the detachable needle assembly 10b with the syringe-mounted locking means 30, and that such telescoping support is self-established by the detachable needle assembly and does not depend to any significant degree, or to any degree whatsoever in the illustrated embodiment, on structural support or interaction of the shield with any elements associated with the syringe 32. Thus, the telescoping support of the needle shield 50b on the needle hub 14b is a substantially self-established attribute of the detachable needle assembly 10b. It is further to be noted that the shield 50b, along its length when in its retracted position, is radially spaced, by the majority of the cross-sectional area of the hub, and in addition by the thickness of the driver member 70b, from corresponding lengthwise portions of the fluid flow path that is established by passages 23b and 28.

The driver member 70b is preferably generally of cylindrical shape as shown and is rotatably mounted on the hub 14b. The driver 70b has a main barrel portion 72b, and a finger wheel 73b. A longitudinal slot 74b and short lateral slots 76b and 78b are formed in and extend through the wall of the barrel portion 72b. The short lateral slot 76b is slightly narrowed at an intermediate point by slight projection 77b as best seen in FIG. 8A. The short lateral slot 78b is similarly slightly narrowed at a similar intermediate point by a similar slight projection whose location is indicated in FIG. 8 by the reference numeral 79b. This latter projection is not illustrated in a separate figure corresponding to FIG. 8A. As shown, the longitudinal slot 74b may extend to the distal or upper edge of the main barrel portion 72b to allow for assembly of the parts. Another similar set of slots is formed in the wall of the main barrel portion 72b diametrically opposite the illustrated slots 74b, 76b and 78b.

Suitable detent, guide and tab means may be provided to hold the shield in its extended or retracted position, to guide its movement between extended and retracted positions, and to allow it to be conveniently manually actuated from the proximate end of the detachable needle assembly. In the illustrated example, a pair of helical grooves is formed in the outer wall of the needle hub 14b. In the drawings, only one of these helical grooves can be seen along its lengthwise extent. This groove is labelled with the reference number 80b and can be seen to extend along and partially around the hub 14b.

The shield 50b is preferably of hollow cylindrical shape as shown, and is the illustrated example has a pair of integrally formed follower fingers 80b extending radially inwardly a short distance at a location near the lower or proximate end of the shield. Each of these fingers extends through one of the slots 74b, 76b, or 78b (depending on the position of the parts) or through one of the counterpart slots at the diametrically opposite side of the hub, and into the helical groove 80b or its counterpart on the opposite sidewall of the needle hub 14b.

The construction as so far described may be supplied in a plastic shell or cover 40b (FIG. 5). The cover may be enlarged at portion 42b to cover the finger wheel 73b and extend past the entire detachable needle assembly. The filleted corners at the top end of the cover may snugly fit against the extended shroud or shield 50b, as shown in FIG. 1. The construction as thus far described may be closed by an end cover 46b attached around the bottom rim of the cover 40b by pressure-sensitive adhesive and provided with a lift tab 48b. This assembly may provide a sterile self-contained package without the need for any additional packaging in a sterile flexible envelope or the like.

When the detachable needle of FIGS. 5-8 is to be used, the user grasps the lift tab 48b and removes the end cover 46b. The user then grasps the cover 40b in the vicinity of the top end of the hub 14b, and connects the assembly to a syringe 32 by inserting the flanges 26b into the threads of the syringe coupler 30 and twisting the hub to tighten the flanges down in the threads until the male member of the coupler is received tightly in the seat 22b. When the detachable needle is tightly coupled to the syringe, the plastic shell or cover is removed by twisting and pulling it off the shroud or shield 50b, leaving the needle in covered or protected condition as illustrated in FIG. 6.

If the cover 40b and end cover 46b are the only packaging for the adjustable needle, the entire exterior of this packaging is not sterile. Even so, sterility of the detachable needle and of the interior passages between the syringe and the needle tip is preserved when the assembly is manipulated and coupled to a syringe in the anticipated and natural manner described above.

It is again noteworthy that the manipulations used to connect the detachable needle of the invention to a syringe are very similar to, if they do not exactly duplicate, the manipulations used to connect the detachable needles of the prior art which are described above. Again, health care workers already familiar with the use of detachable needles require little or no training before they can proceed with confidence to properly connect the detachable needle of the invention. Also again to be noted is the fact that the invention can be used with the same syringes as have been used with the detachable needles of the prior art, without any modifications of such known types of syringes.

When the detachable needle 10b is supplied and is in the condition shown in FIG. 5, the follower finger 82b is positioned at the closed end of the short lateral slot 76b, and the diametrically opposed finger is positioned equivalently in its a short lateral slot diametrically opposed to the slot 76b. The shield 50b is thereby locked against retraction since the follower fingers are not free to travel lengthwise of the hub. After the detachable needle 10b is coupled to a syringe and the cover 40b is removed, the needle may be exposed by pushing the finger wheel 73b to move driver member 70b and therefore move the sides of the short lateral slot 76b past the follower finger 82. (The same relative movement occurs between counterpart elements at the diametrically opposite side of the assembly.) This movement will encounter a resistance because the slight projection 77b must pass the follower finger 82b (the same thing happens with respect to the diametrically opposite counterparts), but the resistance can be overcome with firm finger pressure on the finger wheel 73b to torque the driver member with enough force to compress or deform the slight projection 77b (and its diametrically opposite counterpart) sufficiently to allow the motion to continue. Once the slight projection at each side of the assembly is cleared, the motion can be continued with relatively little resistance.

When the barrel portion has been turned sufficiently to bring the far wall 75b of the longitudinal slot 74b into contact with the follower finger 82b (and to bring the diametrically opposite counterparts into the same relation), the parts are in the position shown in FIG. 6. As the finger wheel 73b continues to be turned, the follower finger, now positioned in the longitudinal slot and under continuing pressure from the wall 75b, is constrained to move downwardly along the associated helical groove 80b (as is its diametrically opposite counterpart) thereby causing the shield 50b to retract (and twist) from the position shown in FIG. 6 to the position shown in FIG. 7. At this position, the follower finger 82b is juxtaposed with the open end of the lower short lateral slot 78b. (The same is true of the diametrically opposite counterparts.) Continued turning of the finger wheel 73b moves the sides of the slot 78b past the finger 82b, resistance caused by the slight projection 79b is overcome, and the movement is continued until the end of the slot 78b is reached. (The same is true of the diametrically opposed counterparts.) This provides an end stop to the turning movement of the driver 70b in the shield-retracting direction. The needle assembly is now locked in shield-retracted or needle-exposed condition.

Again, while the foregoing description of the retracting motions is very detailed, the motions themselves are simple and can be performed in a straightforward and simple manner using a single finger or using the thumb and index finger to turn the finger wheel in a manner that is obvious to the user, or is easily learned if not self-evident. The action is similar to the retracting action of a common lipstick or chapstick, and will therefore "feel" familiar to almost everyone.

After the needle has been used, the shield 50b can be extended to needle covering position by reversing the motions just described. The shield is released from its locked retracted position by finger-applied torquing pressure in the direction opposite to that of the pressure applied during retraction. Sufficient pressure is applied to clear the slight projections 79b (and to do the same with the diametrically opposed counterparts). The remainder of the motion is the reverse of that previously described and should be self-evident.

It is again noteworthy that all manipulations described are performed, so to speak, from the "back" or proximate end of the needle assembly, and the fingers never move past the needle tip, or anywhere close to the needle tip, and never move from a point beyond or in front of the needle tip, but are at all times well away from and "behind" the needle tip.

Another embodiment of the invention is shown in FIGS. 9-12. A detachable needle generally indicated by the reference numeral 10c (FIG. 10) includes a needle proper 12c and a needle hub 14c. The hub 14c is of sufficient diameter so that its lower skirt portion is capable of fitting over the standard locking means 30, as seen in FIGS. 9 and 10. This has the advantage of minimizing the ratio between the overall length of the assembly and the maximum length of telescoping movement between the hub and a shield to be carried on the hub. In other words, for a given designed degree of telescoping movement, lengthwise compactness of the assembly is maximized.

As shown, the hub 14c is preferably of generally cylindrical configuration. The needle 12c is anchored to the hub 14c and extends coaxially from the distal end of the hub. An open mouth in the proximal or lower end of the hub provides inlet means for fluids passing through the hub. The mouth also forms a bore 20c extending upwardly into a seat 22c for receiving the hollow male coupler member 24 associated with a standard coupler of the type previously described. It will be noted that the hollow male coupler member 24 is shown as relatively shorter than in the earlier figures; this shorter male member shown in FIGS. 9 and 10 is believed to more accurately reflect typical relative dimensions of the parts of prior-art standard couplers. From a disclosure standpoint this should be of no significance, since it will be noted that the longer relative dimension shown for the male member of the standard coupler in the first two illustrated embodiments merely affects the longitudinal locations of the seats 22a or 22b, whose longitudinal location obviously can be readily chosen to properly reseat male members of the standard length, whatever that may be.

The hub 14c also has radially extending flange means comprising a pair of radially extending flanges 26c adapted to threadedly engage the interior threads of fitting 30. When the flanges 26c are turned down in the threads, the male coupler member is tightened into the seat 22c, and the central passage 28 of the male coupler member is sealingly connected to the hub passage 23c which leads to the needle 12c, to establish a fluid flow path whose cross-sectional area along almost all, if not all, its longitudinal extent within the hub is a minority of the cross-sectional area of the hub itself.

To save material and weight, the hub 14c is preferably of generally hollow construction as shown, and may be provided with internal stiffening ribs or buttress ribs 15c.

The detachable needle assembly 10c is provided with a shroud or shield 50c which is slidingly supported on the hub 14c for telescoping movement between needle-covering or shield-extended position seen in FIGS. 9 and 11 and needle-exposing or shield-retracted position seen in FIG. 10. In the shield-retracted position, preferably the entire length of the needle outside the hub is exposed, as shown. The portion of the cylindrical exterior of the hub that is underneath the shield constitutes a sliding-fit surface on which the shield is supported in its telescoping movement, and the longitudinal extent of such sliding-fit surface is substantially no less than the distance of travel of the shield between extended and retracted positions. Such sliding fit-surface is not necessarily continuous, but can be interrupted by lightening holes, grooves, chambers, or the like (not shown) for material and weight saving, if desired.

It is to be noted that all points of support of the shield 50c on the hub 14c are themselves supported entirely via the engagement of the screw-down connection means of the detachable needle assembly 10c with the syringe-mounted locking means 30, and that such telescoping support is self-established by the detachable needle assembly and does not depend to any significant degree, or to any degree whatsoever in the illustrated embodiment, on structural support or interaction of the shield with any elements associated with the syringe 32. Thus, the telescoping support of the needle shield 50c on the needle hub 14c is a substantially self-established attribute of the detachable needle assembly 10c. It is further to be noted that the shield 50c, along its length when in its retracted position, is radially spaced, by the majority of the cross-sectional area of the hub, from corresponding lengthwise portions of the fluid flow path that is established by passages 23c and 28.

The detent and guide means provided for the shield 50c includes a guide groove consisting of guide groove segments 91c-96c formed in the shield 50c as best seen in FIGS. 11 and 12. The groove 91c-96c receives a groove follower or detent projection 90c formed on the inner side of the shield 50c. The follower is triangularly shaped, as most clearly seen in FIG. 12A. Barb-like projections 97c are formed in the sidewalls of grooves 92c, 94c and 96c at stations P, Q and R, respectively. The barb-like projections are small and the plastic or plastics forming the parts is somewhat yielding, so that the follower 90c can be forced past the barb-like projections in one direction against the resistance presented by the wedging action between the angled faces of the barb-like projections on the one hand and the angled faces of the follower on the other hand. However, reverse movement is prevented by a locking action between the flat barb faces and the flat face of the follower 90c. When the follower 90c is at station p as shown in FIG. 12A, it is releasably restrained against forward (leftward) movement by wedging engagement with the leftward barb-like projections on either side of the groove 92c, and is locked against rearward (rightward) movement by locking engagement with the rightward barb-like projections on either side of the groove 92c.

This detent and guide means as so far described is duplicated at diametrically opposite sides of the needle assembly 10c, and it is to be understood that the foregoing and following description applies to the detent and guide means at each side, although the elements at only one side may be referred to. For the most part, the views in the drawings are taken in such a way that the detent and guide means at only one side of the needle assembly 10c can be seen in the drawings.

The user manipulates the shield 50c by using one or more fingers to engage or grasp it, preferably at the proximal skirt or lower end of the shield. Such skirt portion constitutes the finger-engageable means for retracting and advancing the shield. To encourage grasping at the lower end, and to improve finger traction, the lower end or skirt of the shield may be knurled, or may be coated or covered, or may otherwise be provided with anti-slip means (not shown).

The construction as so far described may be provided in a sterile pack, with the parts factory-positioned in the position shown in FIGS. 11 and 12A. The groove segment 91c allows insertion of the follower 90c in the guide groove system as part of the assembly procedure. The follower 90c is inserted and the shield is partly turned to snap the follower past the first pair of barb-like projections encountered at station P, but not past the second pair.

When the detachable needle of FIGS. 9-12 is to be used, the user removes the sterile assembly from its sterile packaging, grasps the shield 50c in the vicinity of the lower skirt portion, and connects the assembly to a syringe 32 by inserting the flanges 26c into the threads of the syringe coupler 30 and twisting the hub to tighten the flanges down in the threads until the male member 24 of the coupler is received tightly in the seat 22c. In the course of this tightening, if the twisting forces are sufficient, the follower 90c may come unlocked from the position shown in FIG. 12A and advance to the exiting end (left end) of the groove 92c where it will engage the far wall of groove 92c, whereupon all twisting force on the assembly will be applied to tightening down the hub-to-coupler connection. This is the position of the parts seen in FIGS. 9 and 9A.

When the health care worker removes the needle assembly 10c from its sterile package and handles it, sterility on the exterior of shield 50c and hub 14c may be destroyed, but sterility of the detachable needle and of the interior passages between the syringe and the needle tip is well protected by the container-like configuration of these two elements.

It is again noteworthy that the manipulations used to connect the detachable needle of the invention to a syringe are very similar to, if they do not exactly duplicate, the manipulations used to connect the detachable needles of the prior art which are described above. Again, health care workers already familiar with the use of detachable needles require little or no training before they can proceed with confidence to properly connect the detachable needle of the invention. Also again to be noted is the fact that the invention can be used with the same syringes as have been used with the detachable needles of the prior art, without any modifications of such known types of syringes.

After the detachable needle 10c has been attached, the user uses his or her fingers to pull the shield from the position of FIGS. 9 and 9A to the position of FIG. 10. The user then turns the needle assembly in the same advancing direction as previously used to advance the follower in the groove segment 94c until station Q is reached and the follower snaps past the first set of burr-like projections at that station to reach a condition similar to that shown in FIG. 12 in which the follower 90c is releasably restrained against forward (leftward) movement by wedging engagement with the leftward barb-like projections on either side of the groove 94c, and is locked against rearward (rightward) movement by locking engagement with the rightward barb-like projections on either side of the groove segment 94c (not readily visible on the scale of the drawings, or not visible at all). The shield is thus releasably held against further twisting movement in the advancing direction, and is locked against retrograde movement. Also, the shield is positively locked against movement in the extending or needle-exposing direction by engagement with the upper wall of the groove segment 92a.

After the needle has been used, the shield 50c can be extended to needle-covering position by twisting the shield in the advancing direction with sufficient force to overcome the wedging resistance of the remaining pair of barb-like projections in the groove segment 94c, so that the follower wedges past them and reaches the lower end of the groove segment 95. The shield 50c is then extended to cover the needle whereupon the follower reaches the top end of the groove segment 95c. The shield is then twisted to advance the follower into groove segment 96c and past a first (and only) pair of barb-like projections 97c (not readily visible on the scale of the drawings, or not visible at all) on the opposite side walls of that segment, at which time the follower is locked at final station R and the shield is irreversibly locked in extended position.

It is to be noted that all twisting manipulations occur in a single turning direction, which is the also the tightening-down direction for the connection between the needle assembly 10c and the locking means 30 on the syringe. This continuous one-way movement in the lock-tightening direction to expose and cover the needle avoids the risk of inadvertently releasing the hub from the locking means, or releasing it before the needle is covered.

Again, while the foregoing description of the retracting and advancing motions is very detailed, the motions themselves are simple and can be performed in a straightforward and simple manner using a single finger or using the thumb and index finger to turn, push and pull the shield skirt in a manner that is obvious to the user, or is easily learned if not self-evident. It is again noteworthy that all manipulations described are performed, so to speak, from the "back" or proximate end of the needle assembly, and the fingers never move past the needle tip, or anywhere close to the needle tip, and never move from a point beyond or in front of the needle tip, but are at all times well away from and "behind" the needle tip.

The invention as shown in FIGS. 14–18 is particularly advantageous in many respects. A detachable needle generally indicated by the reference numeral 10d (FIG. 15) includes a needle proper 12d and a needle hub 14d. As shown, the hub 14d is preferably of generally cylindrical configuration. The needle 12d is anchored to the hub 14d and extends coaxially from the distal end of the hub. The distal end of the hub may terminate in four tapered ribs or ears 17d spaced at 90 degree intervals around the hub, as shown, which provide anti-rotation clutch means in association with other elements, as described below.

An open mouth in the proximal or lower end of the hub provides inlet means for fluids passing through the hub. The mouth also forms a bore 20d extending upwardly into a or seat 22d for receiving the hollow male coupler member 24d associated with a standard coupler of the type previously described.

The hub 14d also has radially extending flange means comprising a pair of radially extending flanges 26d adapted to threadedly engage the interior threads of fitting 30. When the flanges 26d are turned down in the threads, the male coupler member is tightened into the seat 22d, and the central passage 28 of the male coupler member is sealingly connected to the hub passage 23d which leads to the needle 12d, to establish a fluid flow path whose cross-sectional area along almost all, if not all, its longitudinal extent within the hub is a minority of the cross-sectional area of the hub itself.

Prior to use, the exposable portion 15d of the needle 12d is covered by a cover cap 40d which is removably and replaceably mounted on support portion 41d of the hub 14d, such support portion being associated with the upper or distal end of the hub. The cover cap 40d has annular flange means generally indicated at 45d and which may, as shown, include a radially extending portion 47d and lip 49d (FIG. 18). The cover cap is preferably tapered as shown to inherently provide stop means to define the fully seated position of the cover cap on the hub. To lock the cover cap and hub together against relative rotation, interference ribs 44d (FIG. 14B) may be provided formed integrally with the cover cap 40b and extending longitudinally a short distance at the same lengthwise portion of the assembly at which the ribs 17d are located. The ribs 44d and 17d thus together provide anti-rotation clutch means when the cover cap 40d is seated on the hub 14d. (Similar tapering and provision of interacting anti-rotation clutch means has been included in prior-art devices such as described above in connection with FIG. 13, but these details are described herein for completeness.)

The detachable needle assembly 10d is provided with a shroud or shield 50d which is slidingly supported on the hub 14d for telescoping movement from retracted position seen in FIGS. 14 and 15 to extended position seen in FIGS. 16 and 17. The shield 50d is supported on support portion 43d of the hub in retracted position and on support portion 41d of the hub in extended position. In the shield-retracted position, the entire length of the needle outside the hub is exposed, as shown. The portion of the cylindrical exterior of the hub that is underneath the shield constitutes a sliding-fit surface on which the shield is supported in its telescoping movement, and the longitudinal extent of such sliding-fit surface is substantially no less than the distance of travel of the shield between extended and retracted positions, and is actually somewhat greater in this embodiment. Such sliding fit-surface is not necessarily continuous, but can be interrupted by lightening holes, grooves, chambers, or the like (not shown) for material and weight saving, if desired.

It is to be noted that all points of support of the shield 50d on the hub 14d are themselves supported entirely via the engagement of the screw-down connection means of the detachable needle assembly 10d with the syringe-mounted locking means 30, and that such telescoping support is self-established by the detachable needle assembly and does not depend to any significant degree, or to any degree whatsoever in the illustrated embodiment, on structural support or interaction of the shield with any elements associated with the syringe 32. Thus, the telescoping support of the needle shield 50d on the needle hub 14d is a substantially self-established attribute of the detachable needle assembly 10d. It is further to be noted that the shield 50d, along its length when in its retracted position, is radially spaced, by the majority of the cross-sectional area of the hub, from corresponding lengthwise portions of the fluid flow path that is established by passages 23d and 28.

The shield 50d is provided with suitable detent and guide whereby (1) the shield is locked, preferably permanently, in its extended position once it is moved to that position, (2) the shield is prevented or stopped from moving beyond its extended position and becoming detached, and (3) the shield is locked against rotation relative to the hub.

Such detent and guide means may include for example two guide grooves 91d formed in the shield 50d as seen in FIGS. 15 and 16. Each groove 91d receives a groove follower or detent 90d molded integrally with the hub 14d and joined thereto by a living hinge whereby the detents 90d may be hinged inwardly into their associated pockets 92d formed in the body of the hub 14d. Each groove 91d terminates at the proximal end of the shield in an endwall 93d (FIG. 16A).

During assembly of the parts, as the shield is slipped over the hub, the outer sides of the endwalls engage the sloping outer sides of the detents 90d to thereby cause the detents to hinge inwardly until the radially inner peripheries of the end walls 93d pass over the detents 90d. As the end walls pass completely over the detents 90d, the latter spring into position in the grooves 91d.

The detent and guide means also include the detents 96d also molded integrally with the hub 14d and each joined thereto by a living hinge whereby the detents 96d may be hinged inwardly into their associated pockets 97d formed in the body of the hub 14d as shown in FIG. 14A.

During assembly of the parts, as the shield is slipped over the hub, the detents 96d may be hinged inwardly with a suitable tool (not shown) to allow the bore of the shield 50d to start to pass over the detents 96d and hinge them into the pockets 97d. The bore of the shield continues to restrain the detents in inwardly hinged condition as assembly of the shield on the hub is then completed by moving the shield downwardly until the bottom end thereof abuts a stop ridge 94d formed near the bottom or proximal end of the hub.

When, during or after removal of the needle from a patient, the shield is moved to its extended position, the bottom end of the shield passes clear of the detents 96d which are then free to spring outwardly their unbiased position and act as a stop against the bottom end of the shield 50d to thereby permanently lock the shield in extended position, as best seen in FIG. 17A. At the same time, the detents 90d engage the inner side of the end walls 93d, as best seen in FIG. 16A, to thereby prevent the shield from moving beyond its extended position and becoming detached from the hub. The engagement of the detents 90d with the sidewalls of the grooves 91d locks the shield against rotation relative to the hub in both the retracted and extended positions of the shield, and during movement of the shield between those positions.

FIG. 15B is a cross-sectional view of a detachable needle assembly very similar to that shown in FIG. 15, and with the parts similarly positioned (except for the omission of a cover cap), illustrating certain alternatives as to hub fabrication and connector fittings.

From a manufacturing standpoint it may be advantageous to fabricate the hub of two elements or more that are welded, sealed, adhered or otherwise permanently combined together, such as elements a and b which form hub 14d' as illustrated in FIG. 15B. Element a is flangeless, and has a cylindrical rather than tapered radially outer surface, but otherwise may have proportions similar to a conventional needle hub, so that it can be manufactured and mount a needle in a similar manner. If the cylindrical outer surface is difficult to provide due to mold draft requirements or other molding constraints, a tapered filler or spacer collar (not shown) can be slipped over a tapered outer surface of element 1, in complementary relationship, to impart a cylindrical outer surface for the support portion 41d of the hub, and the spacer then welded to or otherwise permanently combined with the remainder of the hub.

Element b of hub 14d, may be a solid centrally passaged member as shown on which element 1 is permanently welded or otherwise joined as illustrated. It will be understood that any of the hubs of the various embodiments of the invention can be similarly formed as a similar composite of elements permanently joined together. Also, although illustrated hubs 14a, 14b and 14d are all of solid design radially outwardly of their central passages, any of the hubs may be designed otherwise, as by being provided, say, with lightening holes or grooves (not shown), or, as shown in the case of hub 14c of FIGS. 9-11, by having radially inner and outer portions spaced by a flange or flanges.

FIG. 15B further illustrates a common form of fitting 30' which differs from the fittings 30 shown in the other drawings in that the male member 24' of fitting 30' is gently tapered to be received in a gently tapered seat or socket 22d', rather than bottoming on a sharply angled seat such as seats 22a, 22b, 22c, or 22d, or on a radially extending seat. This is a common form of fitting, and accordingly it will be understood that it may be preferable to modify the shapes of mouths 16a, 16b, 16c and 16d to form gently tapered seats or sockets similar to seat or socket 22d', rather than the sharply angled seats illustrated.

The product of FIGS. 14–18 may be supplied as a sterile package. For this purpose, a cover body 70d may be provided, the mouth of which engages the annular flange means 45d of the cover cap 40d, as seen in FIG. 14. The releasable joint between these parts may be such as to be contamination-proof, or may be covered by a tape, shrink-wrap-label, or the like (not shown) for such purpose and so as to provide tamper-evident means. The cover body 70d, together with the cover cap 40d, provides an outer rigid envelope which encloses and encapsulates the assembly comprising the needle 12d, hub 14d and shield 50d. This rigid envelope mounts such assembly firmly within itself so that the contained parts are anchored and do not rattle around.

A flange (not shown), extending radially from the shield 50d at its lower or proximal end, may be provided, constituting finger-engageable means for powering the advance of the shield from retracted to extended position. Such flange could be at the same longitudinal location as the groove endwall 93d, and may be of arbitrary thickness in the longitudinal direction. If the cover body 70d is used as a packaging element for the device, the radial extent of such flange can be no greater than the inside radius of the cover body, and may match this radius to desirably provide mutual support between the lower end of the assembly and the lower end of the cover body 70d. Such flange can have an arbitrarily large radius if a cover body 70d or like packaging element is not used. It will be noted that such flange would remain remote to the tip of the needle at all times during shield-extending movement. If no such flange is provided, the outer surface of the shield 50d can be knurled, coated, or otherwise treated to improve finger engageability.

When the product of FIGS. 14–18 is to be used, the health care worker removes the cover body 70d from the cover cap 50d by twisting these two cover elements relative to each other to open the joint between them, first removing any tape, shrink-wrap strap or the like. The cover body is then discarded. When the health care worker opens the sterile package and handles the several elements of the assembly, sterility on the exterior of cover cap 40d, shield 50d and hub 14d may be destroyed, but sterility of the detachable needle and of the interior passages between the syringe and the needle tip is well protected by the container-like configuration of these elements.

When the cover body is removed and discarded, the flanges 26d become exposed. Grasping the cover cap 40d near its lower or proximal end, i.e., in the vicinity of the support portion 41d of the hub, the health care worker connects the assembly to a syringe 32 by inserting the flanges 26d into the threads of the syringe coupler 30 and twisting the assembly to tighten the flanges down in the threads until the male member 24 is received in the seat 22d. The necessary twisting force is imparted from the cap to the hub via the anti-rotation clutch means provided by engagement between the ribs 17d and 44d.

The cover cap is then removed by the health care worker by pulling it upwardly away from the hub, exposing the exposable portion 15d of the sterile needle. Medication is then aspirated in the usual manner to fill the syringe 32. If the aspiration is not performed at the patient's bedside, sterile conditions must be maintained while the syringe is transported to the patient. For this purpose, the cover cap is slid over the needle and replaced on the hub, protection against pricking being provided by the annular flange means 47d, behind which the health care worker's thumb and forefinger are naturally positioned as the cover cap is grasped. It is to be further noted that at this stage the needle is still sterile, so that pricking at this time would amount to no more than an inconvenience even were it to occur. It is still further to be noted that this recapping with the flanged cover cap 40d is perfectly consistent with present good practice—that of protecting a sterile needle, following aspiration of medication, by re-covering the needle with a cover cap (non-flanged) such as the cover cap 40, as previously described.

At the patient's bedside, the cover cap, if it has been used to re-cover the needle, is again removed, and the injection is performed. Again, this is perfectly consistent with present good practice. When the injection is completed, and as the needle is removed from the patient, or immediately after removal, the health care worker moves the shield 50d from its retracted to its extended position, by finger engagement with the previously described flange at the lower or proximal end of the shield (not shown), or with the exterior of the shield barrel proper. The shield 50d becomes permanently locked at its extended position by engagement of the detents 96d with the bottom or proximal end of the shield as best seen in FIG. 17A, thus permanently shielding the now-contaminated needle. At the same time, accidental removal of the shield by over-extension is prevented by engagement of the detents 90d with the endwalls 93d of the grooves 91d as best seen in FIG. 16A.

At this point, the shield and hub remain locked against relative rotation by the engagement of the detents 90d with the sides of the slots 91d, as also best seen in FIG. 16A. Thus either the shield or the hub may be grasped to rotate the assembly in the loosening direction to back the flanges 26d out of the syringe-mounted locking means 30 and detach the needle and hub from the syringe. The detachable needle assembly may then be disposed of, the needle remaining shielded by the shield at all times.

Also again to be noted is the fact that the invention can be used with the same syringes as have been used with the detachable needles of the prior art, without any modifications of such known types of syringes.

While presently preferred embodiments of the invention have been described, additions, deletions, modifications and refinements in the invention can be made without departing from the fair teachings thereof. For example, in the product of FIGS. 14–17, the annular flange means 45d can be formed with a skirt extending downwardly over at least the topmost or distal portion of the hub 50d, and the releasable joint between these parts accordingly be located nearer to the bottom or proximal end of the device. The shield may be lightly spring-loaded for extension. The extension-locking detents 96d may be replaced by detents that remain concealed in the extended position of the shield. The scope of the invention is intended to be defined by the following claims, and is not intended to be limited to specific details of the foregoing disclosure except to the extent, if any, fairly required by proper interpretation of the claims.

What is claimed is:

1. A needle and cover assembly comprising a needle hub, said hub having proximal and distal ends, inlet means at the proximal end of the hub for receiving medication from medication-supplying means, a needle anchored to the hub, said needle having an exposable portion extending outwardly from the distal end of the hub coaxially therewith to the tip of the needle, the hub having a cap-receiving portion associated with its distal end, a cover cap removably and replaceably supported on said cap-receiving portion of the hub in covering relationship with said exposable portion of the needle, and a needle shield mounted on the hub, said shield being movable in the longitudinal direction, upon removal of the cover cap from the hub, from a retracted position nearer to said proximal end of the hub, in which retracted position said exposable portion of the needle is exposed, to an advanced position further from said proximal end, in which advanced position the needle shield surrounds said exposable portion of the needle.

2. A device as in claim 1 in which said cover cap has flange means associated with its proximal end for providing a finger guard during replacement of said cover cap on said cap-receiving portion of the hub.

3. A device as in claim 2 said flange means extending radially beyond said needle shield when said cover cap is supported on said cap-receiving portion of the hub.

4. A device as in claim 3 a cover body enclosing the proximal end of said hub and releasably engaging said cover cap, whereby said cover cap and cover body together form a package completely enclosing said hub, needle and shield.

5. A device as in claim 1, a cover body enclosing the proximal end of said hub and releasably engaging said cover cap when said cover cap is supported on said cap-receiving portion of the hub, whereby said cover cap and cover body together form a package completely enclosing said hub, needle and shield.

6. A device as in claim 1, including locking means for locking said needle shield in said extended position upon its advance thereto.

7. A device as in claim 1, including antirotation clutch elements on said cover cap and said hub, said elements being interengageable against relative rotation of said cap and hub when said cover cap is supported on said cap-receiving portion of said hub.

8. In a syringe needle safety assembly, an elongated needle hub, said hub having proximal and distal ends, a needle anchored to the hub at the distal end of the hub, said needle having an exposable portion extending from the distal end of the hub coaxially therewith to the tip of the needle, the hub having a first support portion associated with its distal end and a second support portion between its proximal end and said first support portion, a cover cap removably and replaceably supported on said first support portion of the hub in covering relationship with said exposable portion of the needle, and a needle shield 50d) mounted on said second support portion of the hub, said needle shield being movable in the longitudinal direction, upon removal of the cover cap from the hub, from its retracted position at said second support portion of the hub over said first support portion to an extended position at which at least part of the support of the proximal end of said needle shield is provided by said first support portion and the needle shield surrounds said exposable portion of the needle, said needle shield in its retracted position exposing at least the majority of the length of that portion of the needle which extends from the distal end of the hub.

9. A device as in claim 8 in which said cover cap has flange means associated with its proximal end for providing a finger guard during replacement of said cover cap on said cap-receiving portion of the hub.

10. A device as in claim 9 said flange means extending radially beyond said needle shield when said cover cap is supported on said cap-receiving portion of the hub.

11. A device as in claim 10 a cover body enclosing the proximal end of said hub and releasably engaging said cover cap, whereby said cover cap and cover body together form a package completely enclosing said hub, needle and shield.

12. A device as in claim 8, a cover body enclosing the proximal end of said hub and releasably engaging said cover cap when said cover cap is supported on said cap-receiving portion of the hub, whereby said cover cap and cover body together form a package completely enclosing said hub, needle and shield.

13. A device as in claim 8, including locking means for locking said needle shield in said extended position upon its advance thereto.

14. A device as in claim 8 in which at least a majority of said support of the proximal end of the needle shield is provided by said first support portion.

15. A device as in claim 8, including antirotation clutch elements on said cover cap and said hub, said elements being interengageable against relative rotation of said cap and hub when said cover cap is supported on said first support portion of the hub.

16. A needle and cover assembly comprising a needle hub, said hub having proximal and distal ends and being adapted to be releasably attached to a syringe at its proximal end to thereby support the remainder of the assembly as a self-supported assembly mounted on the syringe via the hub, inlet means at the proximal end of the hub for receiving medication, a needle anchored to the hub at the distal end of the hub, said needle having an exposable portion extending outwardly from the distal end of the hub coaxially therewith to the tip of the needle, a cover cap removably and replaceably supported over the distal end of the hub in covering relationship with said exposable portion of the needle, said support of said cover cap being provided entirely by the remainder of said self-supported assembly independently of any other structure, and a needle shield mounted on the hub, said shield being movable in the longitudinal direction, after removal of the cover cap but independently of and later than said removal, from a retracted position nearer to said proximal end of the hub, in which retracted position said exposable portion of the needle is exposed, to an advanced position further from said proximal end, in which advanced position the needle shield surrounds said exposable portion of the needle, said needle shield in its retracted position exposing at least the majority of the length of that portion of the needle which extends form the distal end of the hub.

17. A device as in claim 16, said removal of the cover cap being free of any linkage or frictional contact with said shield.

18. A device as in claim 16, a cover body enclosing the proximal end of said hub and releasably engaging said cover cap when said cover cap is supported on said remainder of said self-supported assembly, whereby said cover cap and cover body together form a package completely enclosing said hub, needle and shield.

19. A device as in claim 16, including locking means for locking said shield in said advanced position upon its advance thereto.

20. A device as in claim 16, including antirotation clutch elements on said cover cap and said hub, said elements being interengageable against relative rotation of said cap and hub when said cover cap is supported on said remainder of said self-supported assembly.

* * * * *